United States Patent [19]

Strolin-Benedetti et al.

[11] Patent Number: 4,598,084
[45] Date of Patent: Jul. 1, 1986

[54] OPTICALLY ACTIVE DERIVATIVES OF N-ARYLATED OXAZOLIDINE-2-ONE, THE PROCESS FOR PREPARING SAME AND THEIR APPLICATION IN THERAPEUTICS

[75] Inventors: Margherita Strolin-Benedetti, Paris; Patrick G. Guerret, Rueil Malmaison; Michel Langlois, Buc; Philippe L. Dostert, Paris, all of France

[73] Assignee: Delalande S.A., Courbevoie, France

[21] Appl. No.: 500,682

[22] Filed: Jun. 3, 1983

[30] Foreign Application Priority Data

Jun. 8, 1982 [FR] France ................. 82 09972

[51] Int. Cl.$^4$ .................. C07D 263/24; A61K 31/42
[52] U.S. Cl. ..................... 514/374; 548/229; 548/232
[58] Field of Search ............. 548/232, 229; 424/272

[56] References Cited

U.S. PATENT DOCUMENTS 4,287,351  9/1981  Bourgery et al. ............. 548/232

OTHER PUBLICATIONS

Dostert, P. et al., Chem. Abst., 98:46460b (1983).
Strolin Benedetti; M. et al., Chem. Abst., 98:46837e (1983).
Int. Congr. Ser. – Excerpta Med. 1982, 564 Monoamine Oxidase), 197–208.
Int. Congr. Ser. – Excerpta Med. 1982, 564 (Monoamine Oxidase), 209–220.

Primary Examiner—George F. Lesmes
Assistant Examiner—S. A. Gibson
Attorney, Agent, or Firm—Flynn, Thiel, Boutell & Tanis

[57] ABSTRACT

N-arylated oxazolidine-2-one derivatives corresponding to the formula:

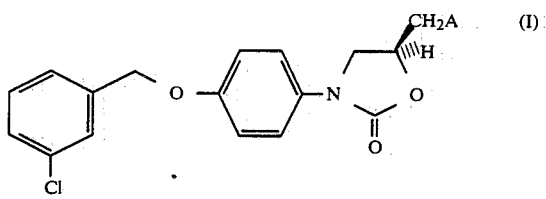

and of S(+) configuration, A representing in this case the hydroxyl radical or of R (+) configuration, A designating then the N-methylamino group, as well as the acid addition salts thereof.

Application in therapeutics more particularly as monoamine oxidase inhibitors.

8 Claims, No Drawings

OPTICALLY ACTIVE DERIVATIVES OF N-ARYLATED OXAZOLIDINE-2-ONE, THE PROCESS FOR PREPARING SAME AND THEIR APPLICATION IN THERAPEUTICS

The present invention relates to new optically active derivatives of N-arylated oxazolidine-2-one, the acid addition salts thereof, the process for preparing same and their application in therapeutics as inhibitors of monoamine oxidase.

At the present time, the use in therapeutics of the so-called "monoamine oxidase inhibitors (M.A.O.I.)" requires the greatest precautions because of their extremely troublesome and dangerous side effects for the patients, particularly: hypertensive crises (related to the ingestion of food containing large amounts of tyramine: "cheese effect" phenomenon); inadequate potentialization of other medicaments administered simultaneously; proscription of associated therapeutic treatment etc.

These side effects are due mainly to the very long duration of action (irreversibility) of these known M.A.O.I.

From French Pat. Nos. 2 381 037 and 2 428 032 are known the compounds of formula:

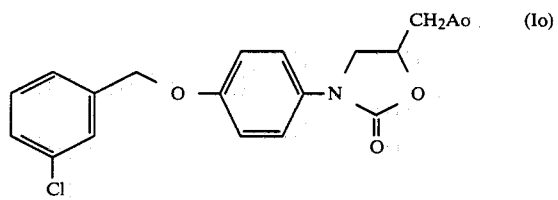

in which Ao represents a hydroxyl radical or a N-methylamino group, these compounds being in the form of racemics.

A thorough pharmacological and biochemical study of these same racemics of formula (Io) has shown that they had activities inhibiting monoamine oxidase. However, their duration of action, although much shorter than that of the known M.A.O.I., still requires precautions during use, which is troublesome for the patient.

The applicant has therefore sought to produce new compounds having a monoamine oxidase and especially type B monoamine oxidase inhibiting activity, at least as good as that of compounds of formula (Io) but not having the above-mentioned disadvantages.

He has thus been led to study the optically active isomers of said compounds of formula (Io) and has found surprisingly that the isomers of the general formula:

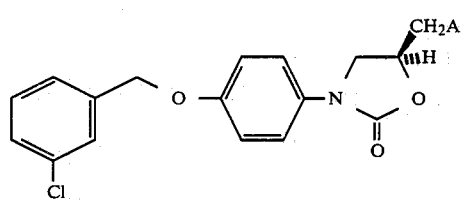

and of configuration S(+), A representing in this case the hydroxyl radical or of configuration R (+), A then designating the N-methylamino group, as well as their acid addition salts, while having a B type monoamine oxidase inhibiting activity similar to that of the corresponding racemics, presented the advantage of a considerably shorter duration of action (irreversibility).

He has further found that these isomers of formula (I) had a much higher specificity than those of the corresponding racemics.

This was demonstrated:

in vitro, on the homogeneized brain of rats, by measuring the dose inhibiting by 50% (IC 50) the activity of monoamine oxidase (MAO) by taking phenylethylamine (PEA) as substrate of type B monoamine oxidase (MAO.B) and serotonine (5-HT) as substrate of type A monoamine oxidase (MAO.A), according to the procedure described by M. STROLIN BENEDETTI et al. in: Monoamine oxidase Basic and Clinical Frontiers, publishers K. KAMISO-E. USDIN-T. NAGATSO-Excepta Medica (1982)-page 209);

ex vivo, on rats to which was administered orally a single dose of the compounds of formula (I) (or their pharmaceutically acceptable salts) or their corresponding racemic of formula (Io), in a 0.5% suspension in methylcellulose, the rats being sacrificed by being beheaded at varying times, the brains being removed, weighed, homogeneized and the determination of the MAOI activity being made by using serotonine and phenylethylamine, according to the procedure described by J. P. KAN and M. STROLIN-BENEDETTI in Life Sciences 26, 2165, (1980).

The results obtained in the in vitro test are shown in table 1 below and the results obtained in the ex vivo test, as well as the oral acute toxicity in mice evaluated according to MILLER and TAINTER's method [Proc. Soc. Exp. Biol. Med. 57, 261, (1944)] are shown in tables 2 and 3 below.

In tables 1 to 3, the compound (Ia) designates that of formula (I) and of particular structure:

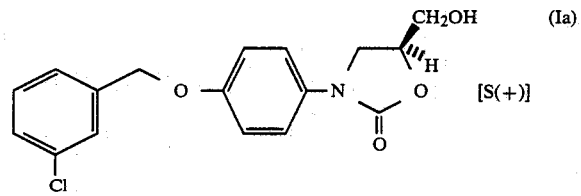

and the compound (Ib) designates that of formula (I) and of particular structure:

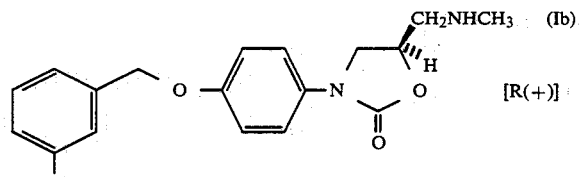

TABLE 1

| Compound tested | MAO.B inhibition effect (P.E.A.) IC 50 (Moles) | (MAO.A inhibition effect (5-HT)) IC 50 (Moles) |
|---|---|---|
| (Ib) | $3 \times 10^{-8}$ M | $5 \times 10^{-5}$ M |
| Racemic of (Ib) | $3.4 \times 10^{-8}$ M | $1.4 \times 10^{-5}$ M |
| (Ia) | $8.5 \times 10^{-8}$ M | $9 \times 10^{-6}$ M |
| Racemic of (Ia) | $2 \times 10^{-8}$ M | $6 \times 10^{-7}$ M |

TABLE 2

| Compound tested | Acute toxicity (mice) LD 50 (mg/kg/p.o.) | Dose (mg/kg/p.o.) | Substrate | % MAO inhibition effect after n hour(s) | | | | | | |
|---|---|---|---|---|---|---|---|---|---|---|
| | | | | 1 | 2 | 4 | 8 | 24 | 48 | 72 |
| (Ib) | >1000 | 5 | PEA (IMAO.B) | 74 | 77 | 71 | 61 | 6 | 5 | 0 |
| | | | 5-HT (IMAO.A) | −1 | 0 | 0 | 1 | −1 | −3 | 3 |
| Racemic of (Ib) | >1000 | 5 | PEA | 84 | 85 | 78 | 67 | 31 | 29 | 21 |
| | | | 5-HT | 7 | 8 | 10 | 8 | 1 | 1 | 1 |

TABLE 3

| Compound tested | Acute toxicity (mice) LD 50 DL 50 (mg/kg/p.o.) | Dose (mg/kg/p.o.) | Substrate | % MAO inhibition effect after n hour(s) | | | | | |
|---|---|---|---|---|---|---|---|---|---|
| | | | | 30 | 1 | 2 | 4 | 8 | 24 |
| (Ia) | >1000 | 5 | PEA | 47 | 47 | 43 | 30 | 5 | −5 |
| | | | 5-HT | 3 | 3 | 2 | 3 | 0 | −2 |
| | | 10 | PEA | — | — | 66 | — | 36 | 6 |
| | | | 5-HT | — | — | 5 | — | 1 | 0 |
| | | 20 | PEA | — | — | 77 | — | 50 | 5 |
| | | | 5-HT | — | — | 7 | — | 3 | 0 |
| Racemic of (Ia) | >1000 | 5 | PEA | 79 | 78 | 79 | 68 | 47 | 1 |
| | | | 5-HT | 21 | 18 | 20 | 9 | 0 | 2 |

It can be seen first of all from these tables that the compound of formula (Ia) and that of formula (Ib) have activities at doses much less than the lethal 50 doses; they may then be used in therapeutics as well as their pharmaceutically acceptable acid addition salts. Moreover, and as these same tables show, the compound of formula (Ib) with a level of activity similar to that of its racemic has a much greater specificity and reversibility. The same goes for the compound of formula (Ia) whose activity increases with the dose administered while keeping a much greater specificity.

This shows the quite unexpected behavior of the compounds of the invention with respect to their respective racemic, a particular behavior which makes the therapeutic use of the compound of formula (Ia), of the compound of formula (Ib) and of their pharmaceutically acceptable acid addition salts by far preferable to that of their corresponding racemics.

The compounds of the invention will be used in troubles of the central nervous system usually treated by means of the type B monoamine oxidase inhibitors, particularly in association with L-DOPA in the treatment of PARKINSON's disease [see for example, Isr. J. Med. Sci. 15, 617, (1979); Adv. in Biochem. Psychopharm. 19, 377; Brit. J. Chem. Pharmacol. 9, 98 (1980)], and in senility troubles.

The invention extends to the pharmaceutical compositions containing, as active ingredient, one at least of the compounds of formula (Ia) or (Ib) or their salts, possibly in association with a pharmaceutically acceptable vehicle.

These compositions will be administered orally, in the form of tablets, pills or capsules at a posology of up to 1 g of active ingredient per day, or in the form of an injectable solution at a posology of up to 200 mg of active ingredient per day.

Besides the aqueous solutions [usable more particularly in the cases of the salts of the compound of formula (Ib)], the solvents used for the injectable forms (particularly for compound Ia), may be formed by binary or ternary mixtures containing for example water, propylene glycol, polyethylene glycol 300 or 400, or any other physiological solvent, the relative proportions of the different constituents of these mixtures being adjusted depending on the dose administered.

The present invention extends finally to the processes for preparing the compounds of the invention.

Thus the compound of formula (Ib) may be prepared: either by optical resolving the corresponding racemic described in French Pat. No. 2 428 032, this resolving being possibly achieved by means of an optically active acid and preferably by means of mandelic acid (+) (dextrorotatory), particularly in a methanol medium, or by action of methylamine preferably in solution in an alcohol such as methanol and in an autoclave, on the compound of formula:

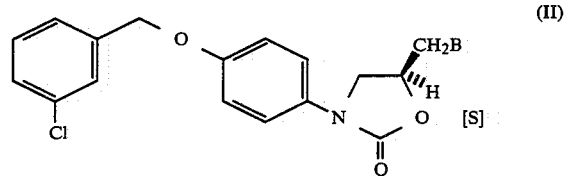

(II)

where B represents a good leaving nucleophile group such as a methylsulfonyloxy or p-tolylsulfonyloxy group. This compound of formula (II) is itself obtained by action of Cl-B (more especially mesyl or tosyl chloride) in the presence of a base preferably triethylamine and in an aprotic medium, preferably methylene chloride, on the compound of formula (Ia).

The compound of formula (Ia) is obtained by the action of metachlorobenzyl chloride in the presence of a base such as potassium carbonate for example, in an aprotic solvent such as methylethylketone for example, and in the presence of a catalytic amount of potassium iodide, on the compound of formula:

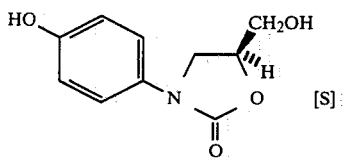

itself obtained by debenzylation, particularly by catalytic debenzylation carried out preferably by means of palladium on charcoal and under a hydrogen pressure, of the compound of formula:

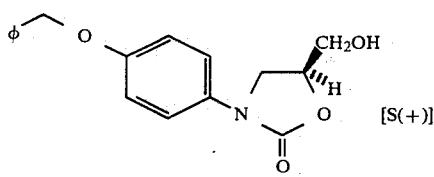

The catalytic debenzylation will be preferably carried out in an autoclave and in the presence of hydrochloric ethanol with possibly heating to temperatures close to 60° C.

The compound of formula (IV) is obtained by cyclization with ethyl carbonate, in the presence of sodium methylate and in an aprotic medium (preferably toluene) of the compound of formula:

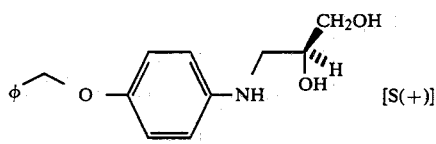

obtained by acid hydrolysis (preferably by means of 1N hydrochloric acid) in an aprotic medium (preferably acetone) of the compound of formula:

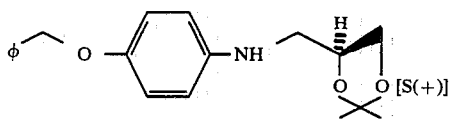

itself obtained by condensation of para-benzyloxyaniline with the compound of formula:

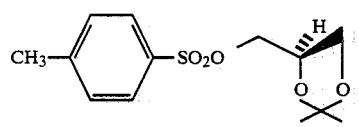

described in J.O.C. 42, 1006, (1977).

The following preparations are given by way of example to illustrate the invention.

EXAMPLE 1

Preparation of [R (+)] 5-N-methyl aminomethyl 3-p-(meta-chlorobenzyloxy)phenyl oxazolidine-2-one methanesulfonate (Ib) by optical resolution of the racemic corresponding to this compound (Ib).

A solution obtained by dissolving, in a heated state, 73.2 g (0.21M) of the racemic corresponding to compound (Ib) and 32.11 g (0.21M) of mandelic acid (+) (dextrorotatory) in 850 ml of ethanol is left at rest for 46 hours. Then the precipitate formed is filtered. Thus 49 g (yield=46.5%) of a precipitate are obtained which is dissolved in 390 ml of ethanol. Then the solution obtained is left to rest for 60 hours and 40.2 g (yield=82%) of a product are obtained by filtration whose melting point is 128° C. This compound is dissolved in 325 ml of ethanol, and it is left to rest for 20 hours and the precipitate formed (38 g) is filtered which is formed by the mandelate of compound (Ib).

Melting point: 130° C.
Empirical formula: $C_{26}H_{27}ClN_2O_6$
Molecular weight: 498.95
$[\alpha]_D^{20} = +70.3°$ (C=1, MeOH)

This compound is then dissolved in water and the resulting aqueous solution is basified by means of NaOH 1N and extracted with methylene chloride. The organic phase is dried on sodium sulfate, filtered and evaporated. Thus 25.86 g of the compound of formula (Ib) are obtained:

Enantiomeric composition: 96-4
Melting point: 75° C.
Empirical formula: $C_{18}H_{19}ClN_2O_3$
Molecular weight: 346.80
$[\alpha]_D^{20} = +42.5°$ (C=1, $CH_2Cl_2$)

This formula (Ib) compound is dissolved in acetone, methanesulfonic acid (1 equivalent) is added to the solution obtained, the whole is cooled to 0° C., the precipitate formed is filtered and recrystallized in 400 ml of ethanol. Thus, 29.7 g (90%) of methanesulfonate of the formula (Ib) compound are obtained.

Melting point: 146° C.
Enantiomeric composition=99.6-0.4
Empirical formula: $C_{19}H_{23}ClN_2O_6S$
Molecular weight=442.91
$[\alpha]_D^{20} = +48.4°$ (C=1, $H_2O$)

EXAMPLE 2 methane sulfonate of [R(+)] 5-N-methylaminomethyl 3-p-(meta-chlorobenzyloxy)phenyl oxazolidine-2-one (Ib).

A solution of 12.3 g of formula (II) compound and 6.5 g of a methylamine saturated methanolic solution in 200 ml of methanol is heated to 110° C. in an autoclave for 1 hour. Then 6 ml of concentrated NaOH are added, the precipitate formed is filtered, the filtrate is diluted with 1 liter of water and extracted with methylene chloride. The organic phase is washed with water, dried on sodium sulfate, filtered and the filtrate evaporated. Thus, 6 g (yield=58%) of formula (Ib) compound are obtained.

Melting point: 75° C.
$[\alpha]_D^{20} = +42.5°$ (C=1, $CH_2Cl_2$)

3.5 g of this formula (Ib) compound is dissolved in 70 ml of acetone and 0.96 g of methanesulfonic acid is added. The solution is cooled to 0° C., the precipitate obtained is filtered and washed with acetone then with isopropylic ether on the filter. Thus, 4 g (yield=91%) of the methanesulfonate of the compound of formula (Ib) are obtained:

Melting point: 146° C.
Empirical formula: $C_{19}H_{23}ClN_2O_6S$
Molecular weight: 442.91
$[\alpha]_D^{20} = +48.9°$ (C=1, $H_2O$)
Elementary analysis:

|  | C | H | N |
|---|---|---|---|
| Calculated (%) | 51.52 | 5.23 | 6.33 |
| Obtained (%) | 51.44 | 5.09 | 6.27 |

EXAMPLE 3

[S] 5-methane sulfonyloxymethyl 3-p-(metachlorobenzyloxy)phenyl oxazolidine-2-one (II)

A solution of 11.5 g of formula (Ia) compound in 200 ml of methylene chloride and 12 ml of triethylamine is cooled to 0° C., then 6.6 ml of methanesulfonyl chloride are added. It is left under agitation at 5° C. for 30 minutes, then the solution is poured into iced water, the precipitate formed is filtered, washed with water, and dried in a vacuum. 12.3 g (yield=87%) of the expected compound are obtained which is used as it is to prepare the formula (Ib) compound according to example 2.

EXAMPLE 4

[S(+)] 5-hydroxymethyl 3-p-(meta-chlorobenzyloxy)-phenyl oxazolidine-2-one (Ia)

To a suspension of 9 g of the compound of formula (III), 20 g of potassium carbonate and a spatula tip of potassium iodide in 200 ml of methylethylketone heated to 60° C. are added 9.5 ml of metachlorobenzyl chloride. Then it is heated at reflux for 3½ hours, diluted with water, filtered, the organic phase is separated by decantation, washed with water, dried on sodium sulfate, filtered and the filtrate evaporated. The residue is recrystallized in absolute alcohol which gives 11.8 g (yield=81%) of the expected compound:
Melting point: 133° C.
Empirical formula: $C_{17}H_{16}ClNO_4$
Molecular weight: 339.76
$[\alpha]_D^{20} = +37.9°$ (C=1, $CH_2Cl_2$)
Elementary analysis:

|  | C | H | N |
|---|---|---|---|
| Calculated (%) | 61.17 | 4.83 | 4.20 |
| Obtained (%) | 61.08 | 4.98 | 4.27 |

EXAMPLE 5

[S] 5-hydroxymethyl 3-para-hydroxyphenyl oxazolidine-2-one (III)

A suspension of 16 g of the compound of formula (IV) and 2.4 g of palladium on charcoal (at 10%) in 500 ml of ethanol and a few drops of hydrochloric ethanol is hydrogenolyzed in an autoclave under a pressure of 6 kg of hydrogen and at a temperature of about 60° C. When the reaction is finished (checked by T.L.C.), the reaction mixture is filtered and the filtrate evaporated. Thus 9 g (yield=80.5%) of the expected compound are obtained (melting point=189° C.) which is used as it is for the synthesis of the compound of formula (Ia) in accordance with example 4.

EXAMPLE 6

[S(+)] 5-hydroxymethyl 3-para-(benzyloxy)phenyl oxazolidine-2-one (IV)

A solution of 2.2 g of the compound of formula (V) and 1.2 ml of ethyl carbonate in 50 ml of toluene is heated at 100°-110° C. for 4 to 5 hours. Then a few drops of sodium methylate in methanol were added. Then it is cooled, the precipitate formed is filtered ans recrystallized in methanol. Thus 1.6 g (yield=66%) of the expected product are obtained:
Melting point: 162° C.
Empirical formula: $C_{17}H_{17}NO_4$
Molecular weight: 299.31
$[\alpha]_D^{20} = +48.2°$ (C=1, $CH_2, Cl_2$)

EXAMPLE 7

[S(−)] 3-para-(benzyloxy)anilino 1,2-propanediol (V)

A solution of 3 g of the compound of formula (VI) in 100 ml of acetone and 10 ml of 1N hydrochloric acid is heated to reflux for 2 hours. Then a few drops of ethanol are added and the solvents are evaporated. The residue is dissolved in water and neutralized with aqueous ammonia. The precipitate formed is filtered, the filtrate is extracted by means of chloroform, the extract obtained is dried on sodium sulfate, filtered and the filtrate evaporated. This residue and the previously formed precipitate are washed with isopropylic ether. Thus 2.5 g (yield ~100%) of the expected product are obtained.
Melting point: 106° C.
Empirical formula: $C_{16}H_{19}NO_3$
Molecular weight: 273.32
$[\alpha]_D^{20} = -14.7°$ (C=1, ethanol)

EXAMPLE 8

[S(+)] 4-para-(benzyloxy)anilinomethyl 2,2-dimethyl 1,3-dioxolanne (VI)

To a suspension of 11.7 g of finely crushed potash in 50 ml of DMSO are added 8 g of the compound formula (VII) then 10.1 g of para-benzyloxyaniline. Then the mixture is heated to 65°-70° C. for 4 hours, then cooled to 10° C. and diluted with 300 ml of water. The precipitate formed is filtered and the filtrate extracted by means of methylene chloride; the precipitate is added to the extract thus obtained, the mixture is washed with water to a neutral pH, dried on sodium sulfate, filtered and the filtrate evaporated. The product obtained is purified by medium pressure liquid chromatography (MPLC) on a silica column (eluent=n-heptane-ethyl acetate mixture: 75-25). The chromatography product is recrystallized in n-heptane and thus 4 g (yield=46%) of the expected compound are isolated.
Melting point: 55° C.
Empirical formula: $C_{19}H_{23}NO_3$
Molecular weight: 313.38
$[\alpha]_D^{20} = +9.17°$ (C=0.24, ethanol).

We claim:
1. A compound having the formula

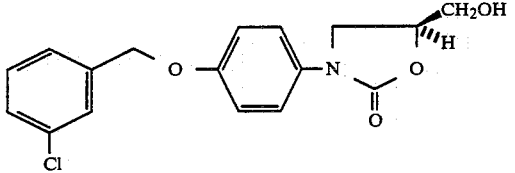

and of S(+) configuration, substantially free of its enantiomer, and pharmacologically acceptable acid addition salts thereof.

2. A pharmaceutical composition having a higher selectivity to type B monoamine oxidase inhibiting activity comprising a compound as claimed in claim 1, in combination with a pharmaceutically acceptable vehicle.

3. A method of treating a patient having a central nervous system disorder that is treatable by type B monoamine oxidase inhibitors, which comprises administering to said patient a therapeutically effective amount of a composition as claimed in claim 2.

4. A method as claimed in claim 3 in which said patient is afflicted with Parkinson's disease.

5. A compound having the formula

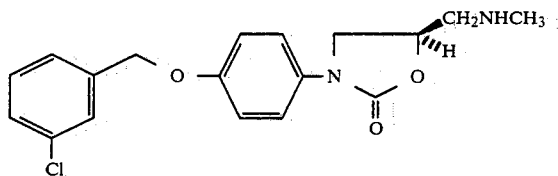

and of R(+) configuration, substantially free of its enantiomer, and pharmacologically acceptable acid addition salts thereof.

6. A pharmaceutical composition having a higher selectivity to type B monoamine oxidase inhibiting activity comprising a compound as claimed in claim 5, in combination with a pharmaceutically acceptable vehicle.

7. A method of treating a patient having a central nervous system disorder that is treatable by type B monoamine oxidase inhibitors, which comprises administering to said patient a therapeutically effective amount of a composition as claimed in claim 6.

8. A method as claimed in claim 7 in which said patient is afflicted with Parkinson's disease.

* * * * *